US008883748B2

(12) United States Patent
Verma et al.

(10) Patent No.: US 8,883,748 B2
(45) Date of Patent: *Nov. 11, 2014

(54) FORMULATION FOR TREATING FUNGAL INFECTION

(75) Inventors: Lily Verma, Haryana (IN); Jitendra Nath Verma, Haryana (IN)

(73) Assignee: Lifecare Innovations Pvt. Ltd., Kolkata (IN)

( * ) Notice: Subject to any disclaimer, the term of this patent is extended or adjusted under 35 U.S.C. 154(b) by 242 days.

This patent is subject to a terminal disclaimer.

(21) Appl. No.: 12/996,870

(22) PCT Filed: Mar. 4, 2010

(86) PCT No.: PCT/IN2010/000125
§ 371 (c)(1),
(2), (4) Date: Jan. 4, 2011

(87) PCT Pub. No.: WO2011/045809
PCT Pub. Date: Apr. 21, 2011

(65) Prior Publication Data
US 2012/0015897 A1 Jan. 19, 2012

(30) Foreign Application Priority Data

Oct. 16, 2009 (IN) .............................. 1258/KOL/09

(51) Int. Cl.
*A61K 31/7048* (2006.01)
*A61P 31/10* (2006.01)
*A61K 9/10* (2006.01)
*A61K 9/127* (2006.01)
*A61K 9/00* (2006.01)
*G01N 1/38* (2006.01)

(52) U.S. Cl.
CPC .............. *A61K 31/7048* (2013.01); *A61K 9/10* (2013.01); *A61K 9/0048* (2013.01); *A61K 9/0014* (2013.01); *G01N 1/38* (2013.01); *A61K 9/127* (2013.01)
USPC .......................................... 514/31

(58) Field of Classification Search
USPC ............................................. 514/31
See application file for complete search history.

(56) References Cited

U.S. PATENT DOCUMENTS

| 4,766,046 A | 8/1988 | Abra et al. |
| 5,032,582 A * | 7/1991 | Abra .............................. 514/31 |
| 5,874,104 A * | 2/1999 | Adler-Moore et al. ........ 424/450 |

FOREIGN PATENT DOCUMENTS

| FR | 2593394 A1 | 7/1987 |
| WO | 2005120460 A1 | 12/2005 |

OTHER PUBLICATIONS

Tremblay et al, Antimicrobial Agents and Chemotherapy, 1984, 26(2), pp. 170-173.*
Rojanapanthu et al, Drug Development and Industrial Pharmacy, 2003, 29(1), pp. 31-37.*
Tremblay, C. et al, Efficacy of Liposome-Intercalated Amphotericin B in the Treatment of Systemic Candidiasis in Mice, Antimicrobial Agents and Chemotherapy, American Society for Microbiology,1984, p. 170-173.
Sculier, J.P. et al. , Pilot Study of Amphotericin B Entrapped in Sonicated Liposomes in Cancer Patients with Fungal Infections, (European Journal of Cancer Clinical Oncology) vol. 24, No. 3, pp. 527-538, 1988.
Rojanapanthu, P. et al, Physicochemical Properties of Amphotericin B Liposomes Prepared by Reverse-Phase Evaporation Method, Drug Development and Industrial Pharmacy, vol. 29, No. 1, pp. 31-37, 2003.
Crowe, J.H. et al, Interactions of sugars with membranes, Biochimica et Biophysica Acta, 947 (1988), pp. 367-384.
Schell, R.E., Amphotericin B—Induced Nephrotoxicity: Influence of Sodium Status, Nephron 1992; 60:252.
Sabra, R. et al., Mechanisms of Amphotericin B-Induced Decrease in Glomerular Filtration Rate in Rats, Antimicrobial Agents and Chemotherapy, Dec. 1991, p. 2509-2514.

* cited by examiner

*Primary Examiner* — Ganapathy Krishnan
(74) *Attorney, Agent, or Firm* — The Webb Law Firm

(57) ABSTRACT

A novel formulation for treating fungal infections comprising Cholesterol containing Nanosomal Amphotericin B in a Saline Suspension.

2 Claims, 2 Drawing Sheets cryoEM images of fresh sonicated (A) and 2 year old sonicated (B) liposome samples. Liposomes with two membrane layers (white arrow) and liposomes with onion-like structure (black arrow). Scale bar represents 200 nm.

cryoEM images of fresh sonicated (A) and 2 year old unsonicated (B) liposome samples showing unilamellar liposomes entrapped within larger unilamellar liposomes (black arrow). Scale bar represents 200 nm.

Fig. 3

FORMULATION FOR TREATING FUNGAL INFECTION

FIELD OF THE INVENTION

The present invention relates to novel drug delivery systems based on nanosomal systems.

In this study samples of cholesterol containing nanosomal Amphotericin B in saline have been studied with cryo-electron microscopy (cryoEM). A fresh and a two year old sample have been analyzed unsonicated as well as after sonication. Analysis of the cryoEM images included size distribution and overall morphology, such as lamellarity (unilamellar versus multilemellar) and aggregation.

BACKGROUND OF THE INVENTION

Rising incidences of Systemic and Topical Mycosis caused by different genus of yeast fungi and dermatophytes in both immuno-deficient and immuno competent patients remain an important and inadequately addressed medical problem. Resulting mortality and alarming prolonged morbidity is of great concern. With all the drugs discovered thus far, there have been problems of limited spectrum, poor potency, limitations of suitable formulations, adverse drug reactions and life-threatening toxicities and quite often a combination of some or all of the above problems. Polyene aminoglycoside group of antibiotics appeared most promising broad-spectrum and potent. However, toxicities of most of these compounds prevented there inclusion as therapeutics.

Amphotericin B has been the only polyene Macrolide that stayed in wide clinical use despite the fact that various formulations such as sodium deoxycholate miceller suspension, liposomal, lipid complex and lipid colloidal dispersion, all contain life-threatening nephrotoxicity to varying extant.

The objectives in formulating Amphotericin B, are to remove nephrotoxicity, make stable preparation, ensure effectiveness at low doses and free of toxicity and adverse drug reactions even at high doses.

Large number of patents granted/filed and publications describing Amphotericin B formulations exist. Except for the below described four formulations no other formulations are operational as they have not been able to make such other formulations adequately nephro/safe.

In all the known Amphotericin B formulations, the constituents are selected from large list of options of phospholipids/lipids and stabilizers. No preparation is infused in saline as Amphotericin B is known to precipitate in saline.

1. Conventional Amphotericin B: Amphotericin B-Deoxycholate colloidal suspension in 5% Dextrose, Efficacy 33% Nephrotoxicity 67%

Amphotericin B is insoluble in aqueous medium. The problem was marginally overcome in late 1950s by dissolving Amphotericin B in deoxycholate and formulating as micellar suspension in 5% dextrose in water. Amphotericin B precipitates in NaCl and thus neither Amphotericin B in deoxycholate was prepared in NaCl nor diluted in saline. Furthermore, this suspension was lyophilized to render stability to the preparation.

2. Liposomal Amphotericin B diluted in 5% Dextrose Efficacy 77% Nephrotoxicity 20%

A Liposomal Amphotericin B made up of combination of soya phosphatidylcholine hydrogenated, distearoylphosphatidylglycerol, cholesterol and alpha tocopherol in 4.5% sucrose and disodium succinate hexahydrate as buffer was selected from amongst number of combinations of phospholipids, sterols, membrane stabilizing sugars and their varying ratios. Despite use of membrane stabilizing sucrose, this preparation was lyophilized to overcome instability. This preparation of Liposomal Amphotericin B is reported to precipitate in saline and thus dilution in/contact with saline is strongly forbidden.

U.S. Pat. No. 4,766,046 describes that:

Due to the size and, instability of Amphotericin B liposomes, it has not been possible to prepare and store small-diameter Amphotericin B liposomes without a significant (several fold) size increase over a several week storage period. As a result, due to different in vivo liposome uptake and drug release and toxicity properties which are related to liposome size, it has been difficult to control and evaluate the therapeutic index of stored Amphotericin B liposomes. The size instability problem is particularly serious where liposome sizes greater than 1-2 microns are attained, since cholesterol-containing Amphotericin B liposomes are substantially more toxic than smaller, original size liposomes. The size stability problem has been solved heretofore only by administering the sized liposomes shortly after preparation. This, of course, is an impractical approach to drug delivery in the usual clinical setting.

3. Amphotericin B Lipid Complex diluted in 5% Dextrose Efficacy 34% Nephrotoxicity 63%

This preparation is composed of Amphotericin B, synthetic phospholipids viz. Dimyristoylphosphatidylcholine and Dimyristoylphosphatidylgycerol. The aqueous suspension is diluted in 5% dextrose before administration. Neither the efficacy nor toxicity profile is improved over conventional Amphotericin B.

4. Amphotericin B Colloidal Dispersion diluted in 5% Dextrose Efficacy 46% Nephrotoxicity 40%

Amhoteric in B and Sodium Cholesteryl Sulphate lyophilized with Tromethamine, Disodium edentate dehydrate and Lactose monohydrate HCl.

Glucose present in Amphotericin B Lipid formulations markedly reduces the beneficial effect of the topically applied formulation. The inhibitory mechanism of glucose is implied to be related to high viscosity introduced by glucose or to changes introduced by glucose on the lipid/water interface of colloidal particles (Crowe J H et. al. 1988 Biochim. Biophys Acta. 947:367-384). Even therapeutic success of Liposomal Amphotericin B at best is 77% which is sub par to present invention.

It was therefore, envisaged to replace dextrose with saline in this invention which has additional advantage of reducing Amphotericin B nephrotoxicity. In view of the well known and documented fact that Saline causes precipitation of Amphotericin B[1-4], lipid composition and lipid to drug ratio were uniquely designed to ascertain that Amphotericin B in the nanosomes is immobilized to prevent precipitation of the nanosomal drug.

OBJECTS OF THE INVENTION

An object of this invention is to provide a novel formulation of cholesterol containing nanosomes stabilized in saline suspension with reduced nephrotoxicity.

Another object of this invention is to propose a novel formulation of cholesterol containing nanosomes stabilized in saline suspension having enhanced antifungal activity.

Still another object of this invention is to propose a formulation of cholesterol containing nanosomes stabilized in saline suspension which is very stable.

Further object of this invention is to propose a novel formulation of cholesterol containing nanosomes stabilized in saline suspension which is less toxic.

Still further object of this invention is to propose a novel formulation of cholesterol containing nanosomes stabilized in saline suspension in which the dose of Amphotericin B used is very little for its high anti-infection activity. Yet another object of this invention is to propose a novel formulation for diverse applications aimed at optimizing lower Amphotericin B doses for higher anti-infective activity, further minimizing nephro/toxicity and stable preparation for various applications such as intra-venous, ophthalmic and topical etc.

BRIEF DESCRIPTION OF THE INVENTION

According to this invention there is provided a novel formulation for treating fungal infection comprising: Cholesterol containing nanosomal Amphotericin B nanosomes in a suspension.

In accordance with this invention, there is also provided a process for preparing the novel formulation of cholesterol containing nanosomes stabilized in Saline suspension.

DETAILED DESCRIPTION OF THE INVENTION

In a solution, the concentration is the number of molecules of the solute in per unit volume of the solvent which in case of injectables and infusions or any other liquid dose form is generally aqueous, whereas in particulate preparations including suspensions such as colloidal suspensions, the effective concentration of the drug is determined by the number of drug carrying particles. Such carriers are diverse nano or micro size assemblies of lipids, proteins or other biodegradable carriers for injectable, oral or inhalable, transdermal etc. and non-biodegradable for topical preparations predominantly. In this invention, nanosomes have an optimally high lipid to drug ratio to increase the number of drug containing nanosomes for each unit quantity of drug and thereby achieving an efficacy optimization by complementing with nanofication before administration.

Optimization of lipid to drug ratio with particulate size is based on novel concept of the present invention in increasing effective concentration of active pharmaceuticals by increasing the number of carrier particles of the API in the formulations post production and prior to administration. This is achieved by reducing the size of the particles of more lipid containing formulation. In the formulation, because of optimally higher lipid to drug ratio there are more number of particles/mg of drug. More particles result in better/higher distribution of drug in the body. As there is more effective concentration of drug in suspension there is more number of molecules distributed evenly throughout the body. This will decrease the requirement of therapeutic dose. As the API for example Amphotericin B is toxic in higher doses, by reducing the requirement of API, will automatically reduce the toxicity to the animals/patients and thus leads to safer drug formulation.

The APIs in the particulate preparation are encapsulated within the multiple layers of the carrier particles. Hydrophobic/lipophilic drugs remain intercalated in the lipid bilayer of lipid nanosomes and therefore not released in aqueous in-vivo environment even upon fragmentation of or breakdown of such nanosomes. Such drugs encapsulated in lipid nanosomes are transferred from surface of nanosomes to the target cell surface. In such an instance, the drugs encapsulated in the inner lamellae of nanosomes are not utilized therapeutically and end up getting phagocitosd by the cells of reticulo-endothelial system and exited from the in-vivo therapeutic chain. The cumulative encapsulation of the drug in the inner lamellae is several times higher than on the nanosomes surface lamella. If all the lamellae of a multilamellar nanosomes are separated to form new small multiple nanosomes the inner lamella encapsulating the drug will thus be converted into outer drug exposing lamella of the nanosomes, it can be logically expected that effective concentration of the drug would increase without any addition of the API to such mix lamellar formulation. This optimization to give higher active concentration for achieving higher therapeutic efficacy would make it possible by subjecting mix lamellar micro and/or nanosomes to ultrasonic disruption on the patients' bedside. From the mix lamellar population each particle makes available several lamella each of which is converted into several nanosomes. By increasing the number of nanosomes, majority of the API in the carrier particles is brought to the surface thus multiplying the therapeutic efficacy in proportion to the increase in the number of drug carrying nanosomes. In the present instance the lipid to drug ratio varies form 45:1 to 45:15. as shown in the table below.

TABLE: 1

Shape and size of different lipid preparations

| Product | Type | Shape | Size | Lipid:Drug | Dose | Nephro-Toxicity |
| --- | --- | --- | --- | --- | --- | --- |
| Nanosomal Amphotericin B in saline | Nanosome | Round | .02-.2 μm | 45:1 | 1-3 mg/kg | 2% |
| AmBisome | Liposomal | Round | .08-.1 μm | 7:1 | 3-5 mg/kg | 10-20% |
| Abelcet | Lipid Complex | Ribbon | 2-5 μm | 1:1 | 5 mg/kg | 42-63% |
| Amphotec | Colloidal Dispersion | Disc | .12-.14 μm | 1:1 | 4-6 mg/kg | 25-40% |

More the lipid matrix: drug means

More are the numbers of liposomes/mg of drug and thus better reach

Nanofication Process:

A novel approach has been innovated to carry out bedside nanofication of the drug in accordance with this invention by using an Ultrasonic processor. This machine allows hand free operation and converts particles into smaller and less lamellar nanosomes resulting in optimally increased therapeutic efficacy through the mechanisms enumerated below.

At the inflammation site the capillaries develop fenestrations and become more permeable which allow movement of cells and particulate substances to migrate/crossover from circulating blood to the surrounding inflamed site. The enhancement of delivery of the drugs in particulate substances to the inflamed areas by fenestration can be facilitated by converting larger carrier particles to nanosomes. Nanofication results in increasing the therapeutic efficacy due to resultant increase in number of drug containing nanosomes concentration at the target site.

Yet another important application of nanofication is to reduce the loss of the larger particles to the phagocytic cells of the reticulo-endothelial system. Larger particles are rapidly identified as foreign particles by the scavenger cells and resultantly are phagocytosed and cleared from the circulation rapidly. The rate of phagocytosis is inversely proportional to the size of drug carrying particles. Therefore, decreasing the size by converting the large and multimellar particles to nanosomes would increase the plasma half-life and delay phagocytic loss thereby further adding to increase in therapeutic efficacy.

The present invention relates to a controlled release pharmaceuticals employing an array of technologies of novel drug delivery systems based on nanosomal systems. In this study samples of cholesterol containing nanosomal Amphoterich B in saline have been studied with cryo-electron microscopy (cryoEM). Fresh and two year old sample have been analyzed unsonicated as well as after sonication. Analysis of the cryo-EM images included size distribution and overall morphology, such as lamellarity (unilamellar versus multilamellar) and aggregation.

The following specific questions were addressed:
size distribution
overall morphology characterization Cholesterol containing nanosomal Amphotericin B in saline samples, fresh and two years old, were imaged using cryoEM. The samples were diluted 10 times and imaged unsonicated and after 45 min of sonication. Sonication was done in an ice-water-bath which kept the temperature of the sample below 8° C.

Size Distribution cryoEM of the diluted nanosome samples showed a very heterogeneous specimen with particles of various morphologies and sizes. The size of the particles varied from 20 nm to micrometer scale in diameter. As might be expected, larger amounts of nanosomes with smaller diameters, 20-200 nm, were seen in the sonicated samples compared to the unsonicated samples. No clear differences could be observed in the cryoEM images between the old and fresh nanosome samples, neither in the unsonicated nor in the sonicated case. Since the samples contained particles with such a wide distribution of sizes and shapes calculating and presenting the means diameters would not be relevant and would only give misleading information.

Overall Morphology

The nanosomes imaged by cryoEm showed well defined membranes with a thickness of approximately 7 nm. The sonicated samples showed a higher degree of small nanosomes which were often seen as separate particles compared to the unsonicated samples where the nanosomes were almost always in contact with each other. The outermost membrane(s) of the unsonicated particles, in both the old and fresh samples, often surrounded more than one nanosome making it hard to differentiate between neighboring nanosomes.

Lamellarity cryoEM showed that the nanosomes appear as both unilamellar and multilamellar. More unilamellar nansomes were found in the sonicated samples compared to the unsonicated samples. The number of membrane layers surrounding the multilamellar particles varied from 2 lamella to onion-like structures with over 10 membrane layers. It also seems as if large particles may entrap smaller ones where the membranes are not in close proximity. However, it is possible that the ice thickness allow these entrapped nanosomes to be spatially located along the z-axis.

Aggregation cryoEM did not show many three dimensional nanosome aggregates in any of the samples. The particles in the unsonicated samples were mainly in close contact and it was often hard to differentiate between where one nanosome ends and another begins since they often shared the outermost membrane layer/layers.

Conclusion

The nanosome samples showed a very heterogeneous specimen with particles of various morphologies and diameters ranging from 20 nm to micrometer scale. Unilamellar nanosomes with smaller diameters, 20-200 nm, were much more frequently seen in the sonicated samples compared to the unsonicated samples. It appears as sonication effectively ruptures the large multilamellar particles seen in the unsonicated samples into small unilamellar nanosomes. Nevertheless, some large multilamellar liposomes were still observed in the sonicated samples and they were often better separated compared to the large multilamellar particles in the unsonicated samples. Prolonged sonication may result in a more Complete rupture of large particles.

There were no clear visible differences between the old versus fresh nanosome samples either comparing the unsonicated or sonicated samples.

Importance of Saline in Reducing AmB Nephrotoxicity

Dose related toxicities particularly nephro-toxicity has been the major impediment in parenteral administration of Amphotericin B. Amphotericin B is known to bind to sterol rich membranes and undergo self-assembled pores formation leading to lysis of these cells. Kidneys being rich in Cholesterol content and Polyene Macrolides such as Amphotericin B having high affinity to cholesterol present a complex scenario limiting use of such compounds as therapeutic agents. Encapsulating Amphotericin B in Cholesterol containing lipid formulation has been of inadequate advantage (see Table 2 below)

| Amphotericin B Formulation | Nephrotoxicity[1] (%) |
|---|---|
| Liposomal Amp B | 10-20 |
| Amp B Colloidal Dispersion | 25-40 |
| Amphotericin B Lipid Complex | 42-63 |
| Amphotericin B Deoxycholate | 34-60[2] |

Furthermore, the apparent remedy to overcome Amphotericin B toxicity by formulating as Saline suspension is being achieved where as earlier Amphotericin has been known to precipitate in Saline. In this invention Amphotericin B has been immobilized in the cholesterol containing matrix preventing mobilization and consequent precipitation. The product of this inventin—Cholesterol containing nanosomal Amphotericin B in Saline suspension drastically lowers nephro-toxicity.

While Ergosterol containing nanosomes would allow higher concentrations of Amphotericin B and would be of value for treatment of Visceral Leishmaniasis only, as provided by this invention replacement of Ergosterol with cholesterol in nanosomal Amphotericin B in Saline suspension is required for potent activity against yeast, moulds and dermatophytes as well as leishmania.

The invention to include saline as a suspension medium is based on the hypothesis that renal function impairment caused by Amphotericin B viz azotemia is associated with a decrease in glomerular filtration rate (GFR) and renal blood flow, reduction in concentration ability, altered urinary acidification, and potassium wasting. Nephrotoxicity of Amphotericin B is related to its ionophore properties on biological membranes. (Schell R E: Amphotericin B induced nephrotoxicity: Influence of Sodium Status (Letter). Nephron 1992; 60:52.)

Glomerular toxicity can develop quickly after a single dose of Amphotericin B or evolve slowly after days to weeks of Amphotericin B therapy depending on the hydration status and underlying renal function of the patient. It is reported that administering intravenous saline before and after Amphotericin B infusions, a practice known as sodium loading blunts the decreases in the Glomerular Filteration Rate caused by Amphotericin B (R Sabra & R A Branch (1991) Mechanism of Amphotericin B-Induced Decrease in Glumerular Filteration Rate in Rats. Antimicrobial Agents and Chemotherapy: 35; 2509-2514).

$LD_{50}$

By increasing the lipid to drug ratio and also the use of saline for suspending the nanosomes has made these nanosomes very safe. During animal preclinical toxicity studies the $LD_{50}$ could not be determined as no animal died up to 60 mg/kg and above 60 mg/kg could not be administered. These nanosomes are ready to use liquid suspension so cannot be administered as concentrated dose and animals could not tolerate higher volume than for a 60 mg dose. It is observed that neither Cholesterol without saline as in Lipsomal Amphotericin B (refer to AmBisome Toxicity/Composition Reference given above) nor Saline without Cholesterol as in Amphotericin B Lipid Complex (refer to Abelcet Toxicity/Composition Reference given above) reduce nephrotoxicity to the insignificant levels as our unique composition of Cholesterol containing high lipid to drug ratio nanosomes in Saline suspension. The in vitro efficacy of Cholesterol containing nanosomal Amphotericin B in saline is many folds higher (at places 10 times) (MIC many fold lower) than the conventional Amphotericin B against the large number of clinical isolates of yeasts and moulds. The reason of higher activity is because these nanosomes as well as the fungal membrane, both have similar and favorable hydro-lipophilic environment so that the transfer of molecule from the nanosome to the fungus is easy.

Stabilizing Nanosomes in Cholesterol & Saline

Stability of Cholesterol containing nanosomal Amphotericin B nanosomes in Saline without any other membrane stabilizing agents, has been made possible by the novel composition of the present invention Nansomal Amphotericin B of the present invention by itself is stable for at least 24 months from the date of manufacture. Thus, it is definite that Cholesterol and Saline plays a major role in increasing the stability of the composition.

EXAMPLES

Example 1

1-15 mg Drug Encapsulation

In the cholesterol containing Nanosomal Amphotericin B in saline, different amount i.e. 1 mg to 15 mg of Amphotericin B per ml could be intercalated successfully without increasing the amount of lipids meaning that for each of 1 to 15 mg/ml of Amphotericin B formulations, quantity of lipids is fixed 45 mg i.e. lipid to drug ratio varies from 45:1 to 45:15.

Determination of "Drug: Lipid ratio in the Nanosomes" and "Amphotericin B in the supernatant" of the innovated formulations:

| Sample Details | Product Code |
|---|---|
| 1 mg/ml- | NAmB-C/1 |
| 3 mg/ml- | NAmB-C/3 |
| 5 mg/ml- | NAmB-C/5 |
| 10 mg/ml- | NAmB-C/10 |
| 15 mg/ml- | NAmB-C/15 |

Amphotericin B assay and residual Methanol contents were determined and results are presented below.

Observations:

(A) Amphotericin B determination in Supernatant liquid

Centrifuged all samples and taken supernatant liquid to perform assay for Amphotericin B. Reading at 405 nm in UV-visible spectrophotometer was found negligible which establishes absence of Amphotericin B in the supernatant liquid meaning that there is no unencapsulated Amphotericin B in the innovated formulation.

(B) Drug: Lipid Ratio in Nanosomes

Determined Drug: Lipid Ratio in the Nanosomes of above formulations.

Observations are given below

| Product code | Concentration | Drug/Lipid Ratio |
|---|---|---|
| NAmB-C/1 | 1 mg/ml | 1:44.6 |
| NAmB-C/3 | 3 mg/ml | 3:44.4 |
| NAmB-C/5 | 5 mg/ml | 5:45.3 |
| NAmB-C/10 | 10 mg/ml | 10:45.01 |
| NAmB-C/15 | 15 mg/ml | 15:45.8 |

Example 2

Relative Nephro-Toxicity of Nanosomal Amphotericin B in Saline v/s Dextrose Suspension Inherent nephrotoxicity of Amphotericin B has been the major obstacle in releasing full potential of this broad-spectrum and potent antifungal drug. Despite known demerits of dextrose on the drug action as elaborated earlier and the possibility of the advantages of saline, dextrose could not be replaced with saline as ironically Amphotericin B is well known to precipitate in saline. The unique design of this nanosomal Amphotericin B has allowed the stable formulation in saline suspension by immobilizing Amphotericin B in nanosomal matrix. To evaluate the nephrotoxicity of dextrose v/s saline the following experiments were carried out.

Experiments were conducted on two groups of swiss albino mice, each group comprised of 6 male and 6 female. One group was administered with saline formulation and another with dextrose at a daily dose of 3 mg/kg for the first 8 days which was further escalated to 5 mg/kg/day for $9^{th}$ and $10^{th}$. Blood was collected on alternate days from half the number of each group of animals and serum creatinine determined from day 2 to day 11 daily.

Individual Animal Clinical Chemistry Data

TABLE 3

Nanosomal Amphotericin B in 5% dextrose
Dose: 3 mg/kg/day
5 mg/kg/day since day 8

| Animal ID | Creatinine mg/dl Day | | | | | | | | | | |
|---|---|---|---|---|---|---|---|---|---|---|---|
| | 0 | 2 | 3 | 4 | 5 | 6 | 7 | 8 | 9 | 10 | 11 |
| Mb4941 | 0.30 | 0.25 | | 0.17 | | 0.22 | | 0.11 | 0.25 | | 0.12 |
| Mb4942 | 0.28 | 0.17 | | 0.25 | | 0.12 | | 0.23 | 0.17 | | 0.19 |
| Mb4943 | 0.16 | 0.15 | | 0.13 | | 0.17 | | 0.34 | 0.25 | | 0.16 |
| Mb4944 | 0.24 | | 0.21 | | 0.22 | | 0.16 | 0.22 | | 0.18 | |
| Mb4945 | 0.12 | | 0.19 | | 0.19 | | 0.17 | 0.16 | | 0.12 | |
| Mb4946 | 0.20 | | 0.23 | | 0.22 | | 0.18 | 0.2 | | 0.22 | |
| Mb4947 | 0.18 | 0.14 | | 0.15 | | 0.19 | | 0.16 | 0.14 | | 0.12 |
| Mb4948 | 0.16 | 0.19 | | 0.10 | | 0.21 | Dead | — | — | — | — |
| Mb4949 | 0.13 | 0.20 | Dead | — | — | — | — | — | — | — | — |
| Mb4950 | 0.14 | | 0.14 | | 0.19 | | 0.25 | 0.12 | | 0.18 | |
| Mb4951 | 0.18 | | 0.17 | | 0.25 | | 0.17 | 0.14 | | 0.06 | |
| Mb4952 | 0.14 | | 0.13 | | 0.24 | | 0.14 | 0.07 | | 0.08 | |
| Mean | 0.19 | 0.18 | 0.18 | 0.16 | 0.22 | 0.18 | 0.18 | 0.18 | 0.20 | 0.14 | 0.15 |
| SD | 0.06 | 0.04 | 0.04 | 0.06 | 0.02 | 0.04 | 0.04 | 0.08 | 0.06 | 0.06 | 0.03 |
| N | 12 | 6 | 6 | 5 | 6 | 5 | 6 | 10 | 4 | 6 | 4 |

Animal ID - Mb4949 - Found dead on day 2 after blood sampling
Animal ID - Mb4948 - Found dead on day 6 after blood sampling

TABLE 4

Nanosomal Amphotericin B in Normal Saline
Dose: 3 mg/kg/day
5 mg/kg/day since day 8

| Animal ID | Creatinine mg/dl Day | | | | | | | | | | |
|---|---|---|---|---|---|---|---|---|---|---|---|
| | 0 | 2 | 3 | 4 | 5 | 6 | 7 | 8 | 9 | 10 | 11 |
| Mb4953 | 0.16 | 0.17 | | 0.20 | | 0.10 | | 0.08 | 0.16 | | 0.15 |
| Mb4954 | 0.21 | 0.19 | | 0.24 | | 0.19 | | 0.15 | 0.13 | | 0.22 |
| Mb4955 | 0.15 | 0.27 | | 0.21 | | 0.12 | | 0.12 | 0.11 | | 0.23 |
| Mb4956 | 0.13 | | 0.09 | | 0.12 | | 0.08 | 0.09 | | 0.02 | |
| Mb4957 | 0.13 | | 020 | | 0.06 | | 0.19 | 0.27 | | 0.13 | |
| Mb4958 | 0.15 | | 0.26 | | 0.15 | | 0.22 | 0.11 | | 0.20 | |
| Mb4959 | 0.12 | 0.19 | | 0.09 | | 0.08 | | 0.08 | 0.11 | | 0.21 |
| Mb4960 | 0.24 | 0.19 | | 0.11 | | 0.11 | | 0.06 | 0.15 | | 0.05 |
| Mb4961 | 0.12 | 0.21 | | 0.14 | | 0.16 | | 0.11 | 0.16 | | 0.24 |
| Mb4962 | 0.13 | | 0.13 | | 0.10 | | 0.04 | 0.22 | | 0.15 | |
| Mb4963 | 0.19 | | 0.18 | | 0.17 | | 0.16 | 0.14 | | 0.27 | |
| Mb4964 | 0.13 | | 0.24 | | 0.12 | | 0.15 | 0.07 | | 0.20 | |
| Mean | 0.16 | 0.20 | 0.18 | 0.17 | 0.12 | 0.13 | 0.14 | 0.13 | 0.14 | 0.16 | 0.18 |
| SD | 0.04 | 0.04 | 0.06 | 0.06 | 0.04 | 0.04 | 0.07 | 0.06 | 0.02 | 0.08 | 0.07 |
| N | 12 | 6 | 6 | 6 | 6 | 6 | 6 | 12 | 6 | 6 | 6 |

No significant differences were observed in serum creatinine levels in either group which necessitated experiments with higher doses and longer duration.

In this experiment two groups of mice each comprised of 50 mice of equal number of males and females. The daily dose was replaced by alternate day administration of a dose of 10 mg/kg, one group was given nanosomal Amphotericin B in 5% dextrose and another in normal saline. For the determination of serum creatinine levels, blood was collected on weekly basis.

TABLE 5

| Nanosomal Amphotericin B | Serum Creatinine Concentration in mg/dl | | | | | | |
|---|---|---|---|---|---|---|---|
| | 0 day | $1^{st}$ wk | $2^{nd}$ wk | $3^{rd}$ wk | $4^{th}$ wk | $5^{th}$ wk | $6^{th}$ wk |
| in 5% Dextrose | 0.19 ± 0.04 | 0.19 ± 0.04 | 0.20 ± 0.04 | 0.21 ± 0.07 | 0.23 ± 0.06 | 0.25 ± 0.07 | 0.25 ± 0.06 |
| in Normal Saline | 0.18 ± 0.05 | 0.18 ± 0.03 | 0.18 ± 0.04 | 0.17 ± 0.04 | 0.17 ± 0.03 | 0.16 ± 0.04 | 0.18 ± 0.04 |

In the dextrose group no significant differences were seen up to $2^{nd}$ week and even subsequently up to six weeks the rise in serum creatinine levels was not significant. Increase in serum creatinine beyond doubling of baseline is seen in 2 animals in $4^{th}$ week, 3 animals in $5^{th}$ week and one animal in $6^{th}$ week. In one animal in the $3^{rd}$ week and in another in 5th week death appears to be related to renal toxicity of the drug. Over all the nephrotoxicity was seen in 14% of the animals.

In the saline group the serum creatinine levels remain consistant throughout the experiment duration of 6 weeks. Only in one animal the rise in serum creatinine level exceeded the doubling of the baseline after 6 weeks of administration. The overall nephro-toxicity is seen in only 2% of cases. 5 of the mice died during the experiment but the death does not seem to be related to the drug.

Example 3

Stabilizing Nanosomes in Cholesterol & Saline

Stability of cholesterol containing Nanosomal Amphotericin B in saline without any other membrane stabilizing agents, for two years has been made possible by unique composition reported in this invention. Real time stability test on finished product

| Product | Cholesterol containing Nanosomal Amphotericin B in Saline. |
|---|---|
| Shelf Life | This Nanosomal Amphotericin B is stable at least 24 months from the date of manufacturing |
| Proposed Expiry | 24 months |
| Storage | Store at 2-8° C. |
| Control Batches | Stability study testing of Nanosomal Amphotericin B was carried out on 3 batches |

| Batch No | Manufacturing Date | Expiry Date |
|---|---|---|
| 50F07-147 | August 2007 | July 2009 |
| 50F07-148 | August 2007 | July 2009 |
| 50F07-149 | August 2007 | July 2009 |

Storage Condition: For long term stability study the products are kept at 2-8° C.

Testing Intervals: The stored samples are withdrawn at predetermined Intervals, the intervals are as follows 0 month 3 month 6 month 12 month 18 month 24 month Real time stability study data of Cholesterol containing Nanosomal Amphotericin B in Saline

| Batch No: | 50F07-147 |
|---|---|
| Manufacturing Date: | August 2007 |
| Expiry Date: | July 2009 |

TABLE 6

| Time | Description | Particulate Matter | Identification | Methanol Content | Lipid Content | Assay |
|---|---|---|---|---|---|---|
| 0 month | Yellow colored suspension | Free from particles | Positive for Amphotericin B | 734.3 ppm | 35.25 mg | 0.996 mg. |
| 3 month | Yellow colored suspension | Free from particles | Positive for Amphotericin B | 733.6 ppm | 35.05 mg | 0.994 mg |
| 6 month | Yellow colored suspension | Free from particles | Positive for Amphotericin B | 732.5 ppm | 34.9 mg | 0.991 mg |
| 12 month | Yellow colored suspension | Free from particles | Positive for Amphotericin B | 730.8 ppm | 34.73 mg | 0.987 mg |

TABLE 6-continued

| Time | Description | Particulate Matter | Identification | Methanol Content | Lipid Content | Assay |
|---|---|---|---|---|---|---|
| 18 month | Yellow colored suspension | Free from particles | Positive for Amphotericin B | 728.5 ppm | 34.5 mg | 0.984 mg |
| 24 month | Yellow colored suspension | Free from particles | Positive for Amphotericin B | 725.0 ppm | 34.2 mg | 0.980 mg |

Real Time Stability Study Data of Cholesterol Containing Liposomal Amphotericin B in Saline

| Batch No: | 50F07-148 |
|---|---|
| Manufacturing Date: | August 2007 |
| Expiry Date: | July 2009 |

TABLE 7

| Time | Description | Particulate Matter | Identification | Methanol Content | Lipid Content | Assay |
|---|---|---|---|---|---|---|
| 0 month | Yellow colored suspension | Free from particles | Positive for Amphotericin B | 720 ppm | 35.5 mg | 0.9976 |
| 3 month | Yellow colored suspension | Free from particles | Positive for Amphotericin B | 718.5 ppm | 35.35 mg | 0.996 |
| 6 month | Yellow colored suspension | Free from particles | Positive for Amphotericin B | 716.8 ppm | 35.25 mg | 0.9952 |
| 12 month | Yellow colored suspension | Free from particles | Positive for Amphotericin B | 712.5 ppm | 35.06 mg | 0.993 |
| 18 month | Yellow colored suspension | Free from particles | Positive for Amphotericin B | 708 ppm | 34.85 mg | 0.9905 |
| 24 month | Yellow colored suspension | Free from particles | Positive for Amphotericin B | 705 ppm | 34.6 mg | 0.988 |

Real Time Stability Study Data of Cholesterol Containing Nanosomal Amphotericin B in Saline

| Batch No: | 50F07-149 |
|---|---|
| Manufacturing Date: | August 2007 |
| Expiry Date: | July 2009 |

TABLE 8

| Time | Description | Particulate Matter | Identification | Methanol Content | Lipid Content | Assay |
|---|---|---|---|---|---|---|
| 0 month | Yellow colored suspension | Free from particles | Positive for Amphotericin B | 744 ppm | 35.4 mg | 1.006 mg |
| 3 month | Yellow colored suspension | Free from particles | Positive for Amphotericin B | 742.5 ppm | 35.3 mg | 1.002 mg |
| 6 month | Yellow colored suspension | Free from particles | Positive for Amphotericin B | 741.4 ppm | 35.15 mg | 0.998 mg |
| 12 month | Yellow colored suspension | Free from particles | Positive for Amphotericin B | 738.8 ppm | 34.95 mg | 0.994 mg |
| 18 month | Yellow colored suspension | Free from particles | Positive for Amphotericin B | 736.0 ppm | 34.7 mg | 0.9905 mg |
| 24 month | Yellow colored suspension | Free from particles | Positive for Amphotericin B | 732.5 ppm | 34.4 mg | 0.988 mg |

Example 4

Comparison of In-Vitro Activity of Conventional Amphotericin B and Cholesterol Containing Nanosomal Amphotericin B in Saline (N Amphotericin B)

The experiments were carried out to determine antifungal spectrum and MIC of Nanosomal Amphotericin B vis-à-vis commonly used antifungals viz.

Amphotericin B, Voriconazole, Itraconazole and Fluconazole to ascertain efficacy against pathogenic yeasts and moulds including dermatophytes.

Following Clinical Isolates Were Tested:

| Fungi | No. of isolates |
| --- | --- |
| Candida albicans | 20 |
| Candida tropicalis | 20 |
| Other Non-albicans Candida | 20 |
| Cryptococcus neoformans | 20 |
| Trichosporon sp. | 10 |
| Zygomycetes | 25 |
| Aspergillus sp. | 25 |
| Dematiaceous hyphomycetes | 20 |
| Fusarium species | 10 |
| Scedodporium sp. | 5 |
| Paecilomyces sp. | 5 |
| Sporothrix schenckii | 10 |
| Penicillium marneffei | 10 |
| Total | 200 |

The in-vitro activity of cholesterol containing Nanosomal Amphotericin B in saline is many folds higher (in some cases 10 times & MIC much lower) than the conventional Amphotericin B against the large number of clinical isolates of yeasts and moulds. Furthermore, Amphotericin B was hitherto known for not being effective against dermatophtes while Nanosomal Amphotericin B is effective against dermatophtes viz. *Trichophyton rubrum, T. tonsurans, T. mentagrophytes, Microsporum gypseum*, and *Epidermophyton floccosum*. The reason of higher activity may be because these nanosomes as well as the fungal membrane, both have similar and favorable hydro-lipophilic environment so that the transfer of Amphotericin B molecule from the nanosome to the fungus is easy.

The observations also support the possibility of lowering the dose when Amphotericin B is administered as cholesterol containing nanosomes. Conventional Amphotericin B which is colloidal suspension of the drug in Sodium Deoxycholate is administered as a daily dose of 1 mg/kg body wt./day while its commercially available lipid formulations developed for overcoming dose limiting toxicity have doses ranging from 3-6 mg/kg body wt./day. High doses effect treatment economics and make the drug unaffordable while the Cholesterol containing Nanosomal Amphotericin B would help lower therapeutic dose and in turn make treatment affordable.

Dermatophytes:
1. *Trichophyton rubrum, T. tonsurans, T. mentagrophytes.*
2. *Microsporum gypseum*
3. *Epidermophyton floccosum*

Fungi Causing Skin Infection:
1. *Candida, Aspergillus, Mucor*

Species Resistant to Azoles:

| | | | |
| --- | --- | --- | --- |
| 1. | *Candida albicans* | N Amphotericin B | Active (0.03-0.25) |
| | | Amphotericin B | Active (0.125-1) |
| | | Fluconazole | Variable (0.125-64) |
| | | Voriconazole | Variable (0.03-8) |
| | | Itraconazole | Variable (0.03-8) |
| 2. | *Cryptococcus neoformans* | N Amphotericin B | Active (0.03-0.25) |
| | | Amphotericin B | Active (0.25-1) |
| | | Fluconazole | Variable (0.125-16) |
| | | Voriconazole | Variable (0.03-16) |
| | | Itraconazole | Intermediate (0.03-4) |
| 3. | *Aspergillus flavus, A. fumigatus* | N Amphotericin B | Active (0.06-0.5) |
| | | Amphotericin B | Active (0.5-2) |
| | | Fluconazole | Resistant (32-64) |
| | | Voriconazole | Active (0.125-1) |
| | | Itraconazole | Variable (0.03-16) |
| 4. | *Aspergillus oryzae* | N Amphotericin B | Active (1-2) |
| | | Amphotericin B | Intermediate (2-4) |
| | | Fluconazole | Resistant (64) |
| | | Voriconazole | Intermediate (0.5-4) |
| | | Itraconazole | Active (0.125-0.5) |
| 5. | *Fusarium* spp. | N Amphotericin B | Active (0.06-0.5) |
| | | Amphotericin B | Active (0.5-1) |
| | | Fluconazole | Resistant (16-64) |
| | | Voriconazole | Intermediate (0.5-4) |
| | | Itraconazole | Resistant (8-32) |
| 6. | *Pseudallescheria boydii* | N Amphotericin B | Active (0.125-1) |
| | | Amphotericin B | Active (0.5-1) |
| | | Fluconazole | Resistant (8-32) |
| | | Voriconazole | Active |
| | | Itraconazole | Active |
| 7. | *Rhizopus arrhizus, R. pusilus* | N Amphotericin B | Active (0.125-0.5) |
| | | Amphotericin B | Active (0.5-2) |
| | | Fluconazole | Resistant (8-64) |
| | | Voriconazole | Variable (1-8) |
| | | Itraconazole | Resistant (8-16) |
| 8. | *Absidia corymbifera* | N Amphotericin B | Active (0.06) |
| | | Amphotericin B | Active (0.5) |
| | | Fluconazole | Resistant (64) |
| | | Voriconazole | Variable (2-16) |
| | | Itraconazole | Resistant (16) |
| 9. | *Mucor* spp. | N Amphotericin B | Active (0.5-1) |
| | | Amphotericin B | Active (1-2) |
| | | Fluconazole | Resistant (64) |
| | | Voriconazole | Resistant (8-16) |
| | | Itraconazole | Resistant (0.03-8) |
| 10. | *Apophysomyces elegans* | N Amphotericin B | Active (1) |
| | | Amphotericin B | Active (2) |
| | | Fluconazole | Resistant (64) |
| | | Voriconazole | Intermediate (8) |
| | | Itraconazole | Resistant (16) |
| 11. | *Curvularia* spp. | N Amphotericin B | Active (0.03-0.125) |
| | | Amphotericin B | Active (0.125-1) |
| | | Fluconazole | Resistant (8-64) |
| | | Voriconazole | Active (1-2) |
| | | Itraconazole | Resistant (8-16) |
| 12. | *Alternaria* spp. | N Amphotericin B | Active (0.25) |
| | | Amphotericin B | Active (1-2) |
| | | Fluconazole | Resistant (32-64) |
| | | Voriconazole | Active (0.5-1) |
| | | Itraconazole | Active (1-2) |
| 13. | *Cladophialophora bantiana* | N Amphotericin B | Active (0.25-0.5) |
| | | Amphotericin B | Active (0.5-1) |
| | | Fluconazole | Resistant (32-64) |
| | | Voriconazole | Active (0.25-2) |
| | | Itraconazole | Active (0.5-2) |
| 14. | *Phialophora verrucosa* | N Amphotericin B | Active (2) |
| | | Amphotericin B | Intermediate (4) |
| | | Fluconazole | Resistant (16) |
| | | Voriconazole | Active (1) |
| | | Itraconazole | Resistant (16) |
| 15. | *Scytalidum dimidatum* | N Amphotericin B | Active (0.03) |
| | | Amphotericin B | Active (0.5) |
| | | Fluconazole | Resistant (32) |
| | | Voriconazole | Active (0.5) |
| | | Itraconazole | Resistant (16) |
| 16. | *Sporothrix schenckii* | N Amphotericin B | Active (0.125-0.25) |
| | | Amphotericin B | Active (0.5-1) |
| | | Fluconazole | Resistant (8-64) |
| | | Voriconazole | Variable (0.03-16) |
| | | Itraconazole | Variable (0.03-16) |

| 17. | Penicillium marneffei | N Amphotericin B | Active (0.125-0.5) |
| | | Amphotericin B | Active (0.25-1) |
| | | Fluconazole | Resistant (32-64) |
| | | Voriconazole | Active (0.25-1) |
| | | Itraconazole | Active (1-2) |
| 18. | Trichophyton rubrum | N Amphotericin B | Active 0.06-0.125 |
| | | Amphotericin B | Active (0.25-1) |
| | | Fluconazole | Variable/Resistant (4-32) |
| | | Voriconazole | Active (0.25-0.5) |
| | | Itraconazole | Resistant (8-16) |
| 19. | Trichophyton mentagrophytes | N Amphotericin B | Active (0.125-0.5) |
| | | Amphotericin B | Active (0.5-2) |
| | | Fluconazole | Resistant (32-64) |
| | | Voriconazole | Active (0.5-1) |
| | | Itraconazole | Active (1-2) |
| 20. | Microsporum gypseum | N Amphotericin B | Active (0.125) |
| | | Amphotericin B | Active (0.5) |
| | | Fluconazole | Resistant (64) |
| | | Voriconazole | Active (0.125-0.5) |
| | | Itraconazole | Active (0.25-0.5) |
| 21. | Paeciliomyces spp. | N Amphotericin B | Variable (0.25-16) |
| | | Amphotericin B | Intermediate (1-4) |
| | | Fluconazole | Resistant (64) |
| | | Voriconazole | Variable (0.125-8) |
| | | Itraconazole | Variable (0.06-16) |

Fluconazole Resistant species: *Microsporum gypseum, Trichophyton mentagrophytes, Trichophyton rubrum, Penicillium marneffei, Sporothrix schenckii, Scytalidum dimidatum, Phialophora verrucosa, Cladophialophora bantiana, Alternaria* spp., *Curvularia* spp., *Apophysomyces elegans, Mucor* spp., *Absidia corymbifera, Rhizopus arrhizus, R. pusilus, Pseudallescheria boydii, Fusarium* spp., *Aspergillus flavus. A. fumigatus, A. oryzae, Paeciliomyces* spp. *Fluconazole Variable* species: *Candida albicans, Cryptococcus neoformans.*

Voriconazole Resistant species: *Mucor* spp.

Voriconazole Variable species: *Sporothrix schenckii, Absidia Corymbifera, Rhizopus arrhizus, R. pusilus, Cryptococcus neoformans, Candida Albicans, Paeciliomyces* spp.

Itraconazole Resistant species: *Trichophyton rubrum, Curvularia* spp., *Fusarium* spp., *Absidia Corymbifera, Mucor* spp., *Apophysomyces elegans, Curvularia* spp., *Rhizopus arrhizus, R. pusilus, Phialophora verrucosa, Scytalidum dimidatum.*

Itraconazole Variable species: *Sporothrix schenckii, Aspergillus flavus, A. fumigatus, Candida albicans, Paeciliomyces* spp.

Nanosomal Amphotericin B variable species: *Paeciliomyces* spp.

Example 5

Figure 1:
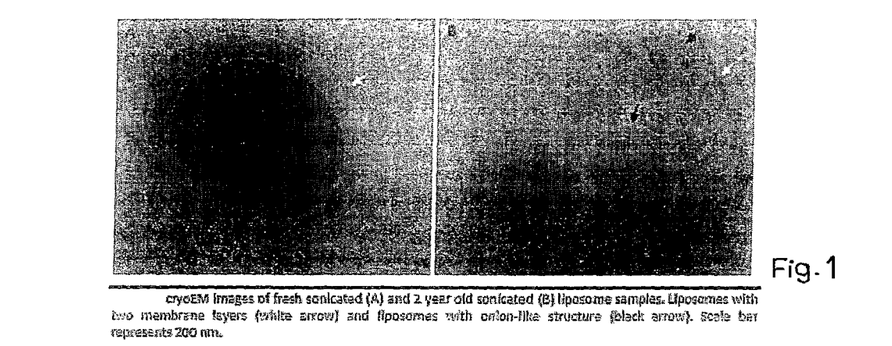
FIG. 1. cryoEM images of (A) fresh sonicated and (B) 2-year old sonicated liposome samples. Liposomes with two membrane layers (white arrow) and liposomes with onion-like structure (black arrows). Scale bar represents 200 nm.
Figure 2:
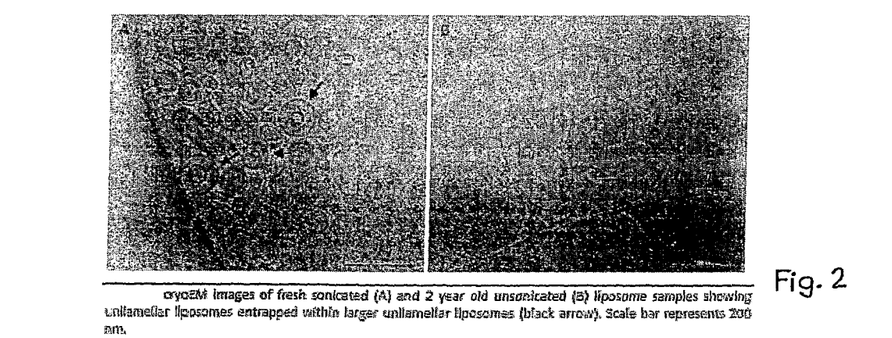
FIG. 2. cryoEM images of (A) fresh sonicated and (B) 2-year old unsonicated liposome samples showing unilamellar liposomes entrapped within larger unilamellar liposomes (black arrow). Scale bar represents 200 nm.

TEM & Freeze Fracture SEM Pre and Post Sonication—Effect of Lipid: Drug Ratio on Particle Count/ml, Effect of Sonication on Particle Count/ml The Nanosome samples showed a very heterogeneous specimen with particles of various morphologies and diameters ranging from 20 nm to micrometer scale. Unilamellar nanosomes with smaller diameters, 20 to 200 nm, were much more frequently seen in the sonicated samples compared to the unsonicated samples. It appears as sonication effectively breaks the large mulitlamellar particles seen in the unsonicated samples into small unilamellar nanosomes. Nevertheless, some large mulitlamellar particles were still observed in the sonicated samples and they were separated compared to the large mulitlamellar particles in the unsonicated samples. Prolonged sonication may result in a more complete breaking of large particles.

There were no clear visible differences between the old versus fresh samples either comparing the unsonicated or sonicated samples. The samples, hence, seem to be stable over the time period (2 years) investigated as shown in FIGS. 1 & 2.

Example 6

Topical Ophthalmic Use of Saline Suspension of Cholesterol Containing Nanosomal Amphotericin B The cholesterol containing Nanosomal Amphotericin B in saline is also studied topically in eyes and found to be safe and effective. *Aspergillus fumigatus* keratitis model treated with Nanosomal and conventional Amphotericin B of different concentration and untreated controls. The results show that half the concentration of Cholesterol containing Nanosomal Amphotericin B in Saline is as effective as conventional Amphotericin B full concentration.

Evaluation of efficacy and toxicity of cholesterol containing Nanosomal Amphotericin B in Saline formulation during treatment of experimental fungal keratitis in rabbit.

Objectives:

a. To evaluate the efficacy of topical Nanosomal Amphotericin B in the treatment of induced fungal keratitis in experimental rabbit model.

b. To compare the efficacy of Nanosomal Amphotericin B at 0.1% and 0.05% concentration with conventional Amphotericin B at 0.1% concentration.

c. To assess any ocular toxicity in rabbit due to treatment with Nanosomal Amphotericin B and compare the same with toxicity due to topical application of Amphotericin B at 0.1% concentration.

Methods

Subjects: New Zealand White rabbits—72

Fungal isolate: *Aspergillus fumigatus* (ATCC 13073), *Candida albicans, Fusarium solani*

*Aspergillus fumigatus* and *Fusarium solani* were grown on a potato dextrose agar slant at 30° C. for 3-10 days. A conidial suspension was prepared by gently swabbing the culture with a sterile swab and transferring it to 3-4 ml of sterile saline in a 15 ml conical tube. Final concentration of conidia was adjusted to obtain $10^6$ conidia/ml. *Candida albicans* was grown on a potato dextrose agar plate for 24 hours at 35° C. Five colonies>1 mm in diameter was picked and suspended in 5 ml of 0.85% sterile saline in a sterile 15 ml conical tube. The suspension was vortexed and cells counted using a hemocytometer. Working suspension of yeast cells was prepared in sterile saline to achieve a final concentration of $10^6$ CFU/ml.

Induction of Keratitis and Treatment

A total of 72 rabbits were used in the study of which 60 rabbits were infected with *Aspergillus fumigatus* inoculum of which 22 rabbits were infected using the contact lens model, while 38 were infected using the intrastromal technique. Eight Rabbits were infected with clinical isolate of *Candida albicans* (4 rabbits with $10^8$ yeast/ml and 2 with $10^9$ cells/ml by intrastromal inoculation and 2 rabbits were infected by using contact lens model with $10^9$ cells/ml). Four rabbits were infected with clinical isolate of *Fusarium Solani* with inoculum dose of ($10^6$ spores/ml) by intrastromal technique.

Induction of keratitis using contact lens: Rabbits were anesthetized with intramuscular ketamine and xylazine. Corneal anesthesia was given using topical proparacaine 0.5%. The nictitating membrane of the right eye was removed by sharp dissection. A 7-mm filter paper disk moistened with 99% isopropyl alcohol (Merck, USA) was placed on the center of the cornea for 30 s and the corneal epithelium was removed atraumatically. The eye was rinsed with sodium lactate solution to remove any remaining traces of isopropyl alcohol. A grid pattern of abrasions was made on the central cornea. The fungal inoculum was transferred to the denuded cornea using a large-bore pipette tip and the inocultum was retained in the cornea by placing the sterile contact lens (diameter, 14.0 mm) (Pure vision, Bosch and Lomb, Ireland). To prevent contact lens extrusion the lids were closed by performing tarsorrhaphy with 5-0 silk sutures. The eyes were examined after 48 hours by removing contact lens and subsequently after every 48 h. Corneal button from each of these rabbits were obtained and subjected to microbiological and histopathological investigation.

Induction of keratitis by intrastromal injection of inoculum: Rabbits were anesthetized with intramuscular ketamine and xylazine. Corneal anesthesia was given with topical Proparacaine 0.5%. 20 1 of fungal inoculum. ($10^6$ spores/1 m) was injected intrastromally using a bent 30 G insulin needle under slit lamp guidance. The rabbits were examined after every 2 days for signs of keratitis.

Evaluation of Antifungals:

Since persistent infection was seen with the model of intrastromal injection of inoculum, the treatment study was carried out with this model. For the treatment rabbits were randomly divided into four groups of each containing 4 rabbits.

The groups inoculated with *Aspergillus fumigatus* were:
Group 1) Treated with 0.1% Nanosomal Amphotericin B,
Group 2) Treated with 0.1% conventional Amphotericin B,
Group 3) Treated with 0.05% Nanosomal amphotericin B
Group 4) Sterile normal saline instillation (untreated controls).

The infections before and after therapy were graded by giving the composite score for different clinical signs determined using with slit lamp microscope. Clinical scores were tabulated for each groups and their mean was taken.

Results
Contact Lens Model:

For the initial standardization of fungal keratitis, of 22 rabbits used eight rabbits were infected with inoculum containing only spores suspension of *Aspergillus fumigatus* by following contact lens model. However, this did not give any clinical or microbiological evidence of infection (both smear and cultures were negative, Table—1). Subsequently fourteen rabbits were infected with a mixture of spores and mycelium, which gave consistent infection in the rabbits as seen in table—1. Although there was consistent clinical infection, the severity of infection reduced after five days. Hence it was not possible to start the treatment on 5th day. Therefore, the intrastromal injection model was adopted for subsequent experiments and the treatment with antifungals was started on the fifth day of infection.

TABLE 9

Results of induction of fungal keratitis in rabbit eyes using contact lens model

| Rabbit ID number | Inoculum used | Clinical feature | Microscopy KOH/ Calcofluor | Fungal Culture | Procedure |
|---|---|---|---|---|---|
| SD-1 | Only Spores | Absent | –ve | –ve | No abrasions |
| SD-2 | Only Spores | Absent | –ve | –ve | No abrasions |
| SD-3 | Only Spores | Absent | –ve | –ve | No abrasions |
| SD-4 | Only Spores | Absent | –ve | –ve | No abrasions |
| SD-5 | Only Spores | Absent | –ve | –ve | Abrasions |
| SD-6 | Only Spores | Absent | –ve | –ve | Abrasions |
| KR-01 | Only Spores | Absent | –ve | –ve | Abrasions |
| KR-02 | Only Spores | Absent | –ve | –ve | Abrasions |
| KR-03 | Spores + mycelium | Absent | –ve | –ve | Abrasions |
| KR-04 | Spores + mycelium | Present | –ve | –ve | Abrasions |
| KR-05 | Spores + mycelium | Present | –ve | +ve | No abrasions with disk |
| KR-06 | Spores + mycelium. | Present | +ve | +ve | Abrasions with disk |
| KR-07 | Spores + mycelium | Present | +ve | +ve | Abrasions with disk + antibiotic |
| KR-08 | Spores + mycelium | Present | +ve | +ve | Abrasions with disk + antibiotic |
| KR-09 | Spores + mycelium | Present | –ve | +ve | Abr. + disk + antibiotic |
| KR-10 | Spores + mycelium | Present | –ve | +ve | Abr. + disk + antibiotic |
| KR-11 | Spores + mycelium | Present | –ve | +ve | Abr. + disk + antibiotic |
| KR-12 | Spores + mycelium | Absent | –ve | +ve | Abr. + disk + antibiotic |
| KR-13 | Spores + mycelium | Present | +ve | +ve | Abr. + disk + antibiotic |
| KR-14 | Spores + mycelium | Present | –ve | +ve | Abr. + disk + antibiotic |
| KR-15 | Spores + mycelium | Present | –ve | +ve | Abr. + disk + antibiotic |
| KR-16 | Spores + mycelium | Present | –ve | +ve | Abr. + disk + antibiotic |

Evaluation of Antifungal Therapy Using Intrastromal Model:

Untreated rabbits had a mean score of 16.1±4.1 SD on day 15. However, 0.1% Nanosomal Amphotericin-B treated rabbits had a mean score of 8.6±2.37 SD, which was statistically significant when compared to the untreated group (p<0.001). Similarly, 0.05% Nanosomal amphotericin-B and 0.1% conventional amphotericin-B treated group had a mean scores of 8.8±2.37 SD and 8.4±2.0 SD respectively.

There was significant difference in the healing when the rabbits were treated with all the three drugs as compared to the untreated group and was statistically significant (p<0.001). However, the composite clinical score of 0.05% Nanosomal formulation is similar to 0.1% of conventional drug for *Aspergillus keratitis*.

TABLE 10

| S. NO | Antifungals | D 0 | D 2 | D 4 | D 5 | D 7 | D 9 | D 11 | D 15 |
|---|---|---|---|---|---|---|---|---|---|
| | | Mean clinical composite score (n = 38) | | | | | | | |
| 1 | 0.1% Nanosomal Amphotericin B | 0 | 7.2 | 13.1 | 13.6 | 14.88 | 14.23 | 12.05 | 8.66 |
| 2 | 0.05% Nanosomal Amphotericin B | 0 | 8.35 | 13.43 | 13.7 | 14.45 | 13.1 | 10.78 | 8.8 |
| 3 | 0.1% Conventional Amphotericin B | 0 | 8.3 | 13.6 | 14.5 | 14.5 | 12.3 | 11.5 | 8.4 |
| 4 | Untreated controls | 0 | 8.4 | 14.4 | 16.1 | 16.5 | 16.1 | 16.3 | 16.1 |

Example 7

Experimental Evidence of Innovatively Designed "Phospholipids-Cholesterol Nanosome Mediated Dermal Delivery of Amphotericin B"

Amphotericin B well known for not being absorbed through skin has limited development of an effective topical formulation that has been overcome by this invention by encapsulating Amphotericin B in innovated Cholesterol/Phospholipid Nanosomes. The penetration and dermal delivery of nanosomes encapsulated Amphotericin B may well be accounted to the Cholesterol-Phospholipid Nanosome specific advantages, i.e., interaction of phospholipids with intercellular lipids; presence of moisture in conjunction with lipids; and the changes in physicochemical properties, such as solubility and partitioning of the Amphotericin B molecules as desired. Further, as observed, the achieved retention of Amphotericin B in skin on topical application of nanosomal Amphotericin B in innovated formulation is one of the most sought after behavior for improved drug-receptor interaction as well as for protracted action of Amphotericin B.

The results, as obtained after study of the skin permeation behavior and fluorescent marked photographic analysis, convincingly points towards the superiority of the Nanosomal Amphotericin B formulation vis-à-vis conventionally prepared Amphotericin B cream. This forms the basis of the novelty in the Nanosomal Amphotericin B for topical dermal delivery of Amphotericin B.

Objectives:

To study the influence of Cholesterol containing nanosomes in Saline formulation on the dermal delivery of Amphotericin B in comparison to conventional Amphotericin B cream-Development of suitable study medium for permeation studies Method development and validation for analysis
In-vitro permeation studies using Franz diffusion cell
Determination of drug-skin retentively
Monitoring of drug transportation (fluorescence marked studies)

Amphotericin B comes under the BCS class IV drugs, hence is difficult to penetrate into any biological barrier including skin. The various reasons includes are as follows:

Drug specific problems
Solubility
Partitioning
Skin specific problem (Tough horny keratin barrier)
Drug-Skin interactions
Improper interactions due to the difference in physico-chemical properties of the drug and skin Despite earlier attempts to make useful topical application, the bulky molecule of Amphotericin B, is difficult for absorption through the skin. As a result, none could successfully achieve the goal. The fundamental problem of molecule is its physico-chemical property as well as skin barrier. This provides a rational to explore the potential of nanosomal system for topical delivery. Herein the hypothesis is based on the principle that the drug within the aqua-lipoidal vesicular milieu would acquire a different physicochemical set of properties to interact favorably, in-order to migrate deeper into the skin layers. The moisture within the vesicles, along with lipidic-molecule, is the key role player in the improved drug transfer vis-à-vis conventional systems. Besides this, integration of phospholipids with skin lipids helps build conducive milieu for improved delivery.

Methodology

Diffusion and Retention studies—Skin permeation of Amphotericin B using different carrier systems were studied using a Franz diffusion cell. The effective permeation area of the diffusion cell and receptor cell was 3.14 cm$^2$ and volumes of the respective cells were 10 ml and 30 ml. The temperature of receptor fluid was maintained at 32±1° C. The receptor compartment contained Briz-35 (5%)+Docusate Sodium (DOS) (1%) in distilled water to facilitate sink condition.

Abdominal skin of male Laca mice (4 to 6 weeks old) was mounted, after hair removal and de-fatting the skin, between the donor and receptor compartment. Formulation equivalent to 358.5 µg (nanosomal/conventional cream) was applied on donor compartment, after equilibrating the skin with sink medium for 2 hr. Samples (1 ml) were withdrawn through the sampling port of the receptor compartment, with replacement, at predetermined interval and analyzed by UV spectrophotometer after suitable dilution.

Fluorescent marked migration study—Inherent fluorescent character of the Amphotericin B has been exploited to visualize the migration and localization of the drug with time. Laca mice were shaved using hair removing cream a day before the study. Mice were scarified humanely at predetermined interval and, immediately skin was washed with PBS pH 7.4 and stored in 10% formalin at −20° C. till cryo-microsectioning. The sections were viewed under fluorescence microscope with F2 filter.

Observations

Diffusion and Retention studies—A range of solvent systems were tried and finally a system composed of Briz-35 (5%) Docusate Sodium (1%) was chosen as a sink media. The objective of this study was to access the penetration, retention and permeation of the drug into, at and across the skin layers respectively. The major observation is that there is appreciable drug retention within the layers of skin after nanosomal application (i.e. 1.291±0.04) vis-à-vis conventional cream (0.142±0.05). However, with regards to permeation, the drug Amphotericin B failed to permeate across the skin layers (in both the cases of nanosomal and conventional systems) is insignificant as shown in FIG. 3.

Figure 3:
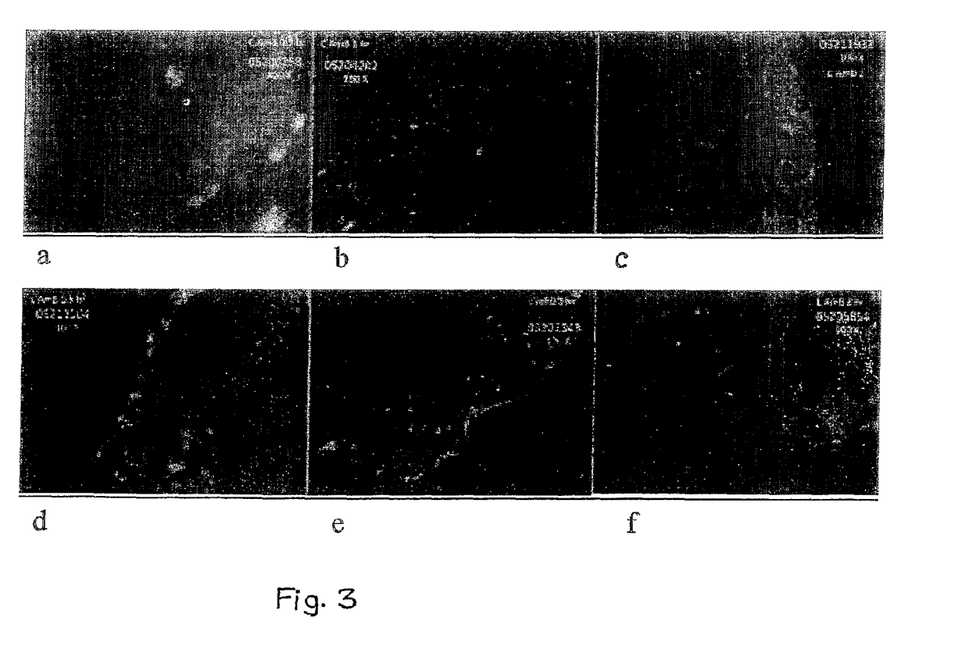
FIG. 3. Fluorescent transverse section of skin after the application of (a) conventional Amphotericin B cream at 0.5 hr; (b) conventional Amphotericin B cream at 1.0 hr; (c) conventional Amphotericin B cream at 2.0 hr; (d) nanosomal Amphotericin B formulation at 0.5 hr; (e) nanosomal Amphotericin B formulation at 1.0 hr; and (f) nanosomal Amphotericin B formulation at 2.0 hr.

FIG. 3. Fluorescent transverse section of skin after the application of (a) conventional Amphotericin B cream at 0.5 hr; (b) conventional Amphotericin B cream at 1.0 hr; (c)

conventional Amphotericin B cream at 2.0 hr; (d) nanosomal Amphotericin B formulation at 0.5 hr (e) nanosomal Amphotericin B formulation at 1.0 hr (f) nanosomal Amphotericin B formulation at 2.0 hr.

TABLE 11

Drug release and retention of Amphotericin B-

| S. No. | Formulation | Media used | % Drug Permeation | Drug retained (μg per sq. cm) |
|---|---|---|---|---|
| 1 | Nanosomal Amphotericin B | 5% Briz35 + 1% DOS in DW | 0.3 ± 0.015 | 1.291 ± 0.04 |
| 2 | Conventional Amphotericin B cream | 5% Briz35 + 1% DOS in DW | 0.1 ± 0.017 | 0.142 ± 0.05 |

Fluorescent marked migration study—The fluorescent marked study (after application of conventional and nanosomal formulations) to monitor the penetration of drug in the skin layer has been shown in FIG. 1. It comprises the monitoring at different time intervals, i.e., 0.5, 1.0, 2.0 hrs. The study revealed an appreciable difference at these intervals. The most remarkable difference was found after 2 hrs of study.

The outcome of permeation behavior studies (Franz diffusion cell) and penetration studies (fluorescent marked skin-histology studies) points to the ability of the nanosomal vesicles to improve the delivery of Amphotericin B. As shown by the drug retention data as well as 2 hr picture of skin-histology, the Amphotericin B contained in the nanosomes is able to penetrate appreciably in comparison to conventional drug formulation. The poor permeation of nanosomal Amphotericin B as well as conventional drug formulation reveals that the drug does not get across the skin layer and hence is not fit for the transdermal drug Amphotericin B delivery. Henceforth, the Amphotericin B in nanosome has shown a good potential for dermal delivery. The poor penetration even serves as an advantage, as it does not allow the Amphotericin B to be systemically absorbed.

We claim:

1. A formulation for treating fungal infections consisting essentially of Amphotericin B encapsulated in a phospholipid and cholesterol nanosome in a saline suspension, wherein the suspension is dilutable only in saline, and wherein the lipid to Amphotericin B ratio is 45:1.

2. The formulation as claimed in claim 1, wherein the Amphotericin B is sonicated to convert the particles into smaller and less lamellar nanosomes within diameters 20-200 nm.

* * * * *